United States Patent [19]

Hecht et al.

[11] 4,282,361

[45] Aug. 4, 1981

[54] SYNTHESIS FOR 7-ALKYLAMINO-3-METHYLPYRAZOLO[4,3-D]PYRIMIDINES

[75] Inventors: Sidney M. Hecht, Newtonville, Mass.; Ulrich Jordis, Vienna, Austria

[73] Assignee: Massachusetts Institute of Technology, Cambridge, Mass.

[21] Appl. No.: 887,383

[22] Filed: Mar. 16, 1978

[51] Int. Cl.$^3$ .................. A61K 31/505; C07D 487/04
[52] U.S. Cl. ..................................... 544/262; 424/251; 548/373; 548/375; 548/377
[58] Field of Search ........................................ 544/262

[56] References Cited

U.S. PATENT DOCUMENTS

| | | | |
|---|---|---|---|
| 2,980,677 | 4/1961 | Druey et al. | 544/262 |
| 3,682,957 | 8/1972 | Cresswell et al. | 544/262 |
| 3,939,161 | 2/1976 | Ratajczky et al. | 544/262 |

FOREIGN PATENT DOCUMENTS

1326360 8/1978 United Kingdom ..................... 544/262

OTHER PUBLICATIONS

Lucas, *Organic Chemistry,* 2nd ed., 1953, Amer. Book Co., N. Y., pp. 175, 223–226, 370–371.
Robins, et al., "Jour. of Org. Chem.", vol. 21, No. 8, 1956, pp. 833–836.

*Primary Examiner*—Donald G. Daus
*Assistant Examiner*—James H. Turnipseed
*Attorney, Agent, or Firm*—Arthur A. Smith, Jr.; David E. Brook

[57] ABSTRACT

An improved synthesis is disclosed for 7-alkylamino-3-methylpyrazolo[4,3-d]pyrimidines, which are known to be potent cytokinin antagonists.

4 Claims, No Drawings

SYNTHESIS FOR 7-ALKYLAMINO-3-METHYLPYRAZOLO [4,3-D]PYRIMIDINES

BACKGROUND OF THE INVENTION

1. Field of the Invention

This invention is in the field of organic chemistry.

2. Description of the Prior Art

Cytokinins are a generic class of substances which promote cell division and growth and which occur at the purine, ribonucleoside and ribonucleotide levels in plants, as well as in the transfer RNA's of most forms of life. See Skoog, F. and Armstrong, D. J., *Ann. Rev. Plant Physiol.,* 21, 359 (1970).

There are other classes of compounds which have more recently been synthesized which are structurally related to cytokinins, but act as cytokinin antagonists or anticytokinins in certain plant bioassays. It is postulated that such cytokinin antagonists could be employed to regulate plant development and the biosynthesis of specific products such as proteins, vitamins, chlorophyll and other compounds which the plant uses, for example, in energy metabolism and in adjustment to its environment. In addition, such cytokinin antagonists might be used to study plant cell genetics because they are an appropriate means to prevent mitosis or cytokinesis while manipulating cells to cause cell fusions or differentiation. These cytokinin antagonists can be used alone or in combination with cytokinins to interrupt, for short periods of time, the normal cytokinin effects on growth, etc.

It has also been disclosed that cytokinin antagonists can be used to achieve certain physiological effects in animal cells. For example, in U.S. patent application Ser. No. 740,287, filed Nov. 9, 1976, it is disclosed that cytokinin antagonists can be used to regulate intracellular levels of cyclic AMP. In U.S. patent application Ser. No. 674,003, filed Apr. 5, 1976, it is disclosed that one cytokinin antagonist, namely 3-methyl-7-n-pentylaminopyrazolo[4,3-d]pyrimidine, is a particularly potent regulator for human cells which are growing, such as PHA-transformed human lymphocyte cells.

Although there are several classes of compounds which have been described as possessing cytokinin antagonist activity, the class of 7-alkylamino-3-methylpyrazolo[4,3-d]pyrimidine compounds is still one of the more important. The cytokinin antagonist activity of this class is particularly described in U.S. patent application Ser. No. 285,677, filed Sept. 1, 1972 now abandoned.

Despite their increasing importance, it has previously been impossible to produce these compounds in high yields, reasonable amounts, and good purity because of the problems encountered with all known syntheses. For example, 3-methyl-7-n-pentylaminopyrazolo[4,3-d]pyrimidine was first synthesized by displacement of the S-methyl group of 3-methyl-7-methylthiopyrazolo[4,3-d]pyrimidine with n-pentylamine. See Skoog, F. et al, *Phytochemistry,* 72, 25 (1973). Although the desired antagonist could be obtained in fairly good yield from this reaction, it had to be purified on a chromatographic column. Additionally, some of the precursors to the 7-methylthio analogue were obtainable only in moderate yields, which lowered the overall yield for the complete synthesis to the order of only about 1%. In addition to this low overall yield, the resultant product had only fair purity. Additionally, and possibly more seriously, this synthetic scheme could only be carried out on a very small scale and did not lend itself to being scaled up to produce reasonable quantities of product.

SUMMARY OF THE INVENTION

The invention comprises a new synthetic scheme for producing 7-alkylamino-3-methylpyrazolo [4,3-d]pyrimidines. In this scheme, 3-methyl-4-nitropyrazole-5-carboxylic acid is esterified to produce ethyl 3-methyl-4-nitropyrazole-5-carboxylate. This can be done, for example, using an alcoholic solution of the acid which is saturated with hydrogen chloride and carrying the reaction out at room temperature to minimize concomitant alkylation of the pyrazole nucleus.

The acid compound, namely 3-methyl-4-nitropyrazole-5-carboxylic acid can be produced by condensation of 2,5-pentanedione with hydrazine hydrate to produce 3,-5-dimethylpyrazole. This compound can be nitrated with a mixture of nitric acid and sulfuric acid and subsequently oxidized to the acid with potassium permanganate, or the oxidization and nitration steps can be done in the reverse order.

Ethyl 3-methyl-4-nitropyrazone-5-carboxylate is transformed to its 5-carboxamide analogue, which can be done, for example, by reacting the ester with ammonium hydroxide. This 5-carboxamide analogue is then catalytically reduced and formylated to produce 4-formylamino-3-methylpyrazole-5-carboxamide. Catalytic reduction can be achieved with hydrogen in the presence of palladium and carbon, whereas formylation can be achieved with a solution of formic acid, ethanol and water. Catalytic reduction and formylation can be done simultaneously or as separate transformations.

An intramolecular ring closure is then performed to produce a pyrazolo[4,3-d]pyrimidine nucleus. This can be done by introducing 4-formylamino-3-methylpyrazole-5-carboxamide into refluxing dimethylformamide containing a catalytic amount of sodium methoxide to produce 7-hydroxy-3-methylpyrazolo[4,3-d]pyrimidine in high yield and excellent purity.

The 7-hydroxy compound is subsequently transformed to the 7-chloro analogue which can be reacted with an alkylamino compound to yield the desired 7-alkylamino-3-methyl-pyrazolo[4,3-d]pyrimidine compound.

This synthetic scheme produces much higher overall yields than other known schemes. The overall yields, for example, are in the order of 20% and higher. In addition, the chromatographic separations required in other schemes are not required, and yet excellent product and precursor purities are obtainable. Most importantly, the scheme can be scaled up so that reasonable quantities of the end product can be produced.

DESCRIPTION OF PREFERRED EMBODIMENTS

Each of the transformations in this synthetic scheme, as well as the preparation of starting materials, will not be described in more detail.

Synthesis of 3-methyl-4-nitropyrazole-5-carboxylic acid 3-methyl-4-nitropyrazole-5-carboxylic acid is the starting material in this synthetic scheme for producing 7-alkylamino-3-methylpyrazolo[4,3-d]pyrimidine compounds. Typically, this acid has been produced by nitration of 3-methylpyrazolo-5-carboxylic acid, which has been synthesized by cyclization and saponification of the sodium salt of ethyl acetylpyruvate. Since the isolation and yield of this sodium salt has been somewhat troublesome, a different route has been devised.

Thus, 3-methyl-4-nitropyrazole-5-carboxylic acid was prepared by the condensation of 2,5-pentanedione with hydrazine hydrate to afford 3,5-dimethylpyrazole. See *Organic Synth. Coll. IV*, page 351. Potassium permanganate is then used to oxidize this 3,5-dimethylpyrazole to the acid, which is then nitrated with nitric and sulfuric acids to form a very pure form of 3-methyl-4-nitropyrazole-5-carboxylic acid. Alternatively, the oxidation and nitration steps can be reversed. These reactions can be illustrated as follows:

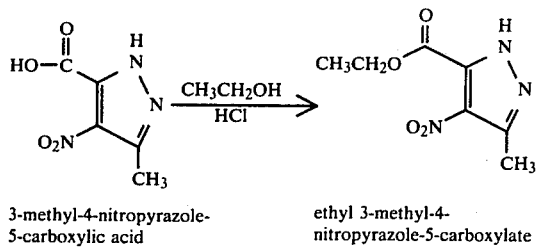

Transformation to

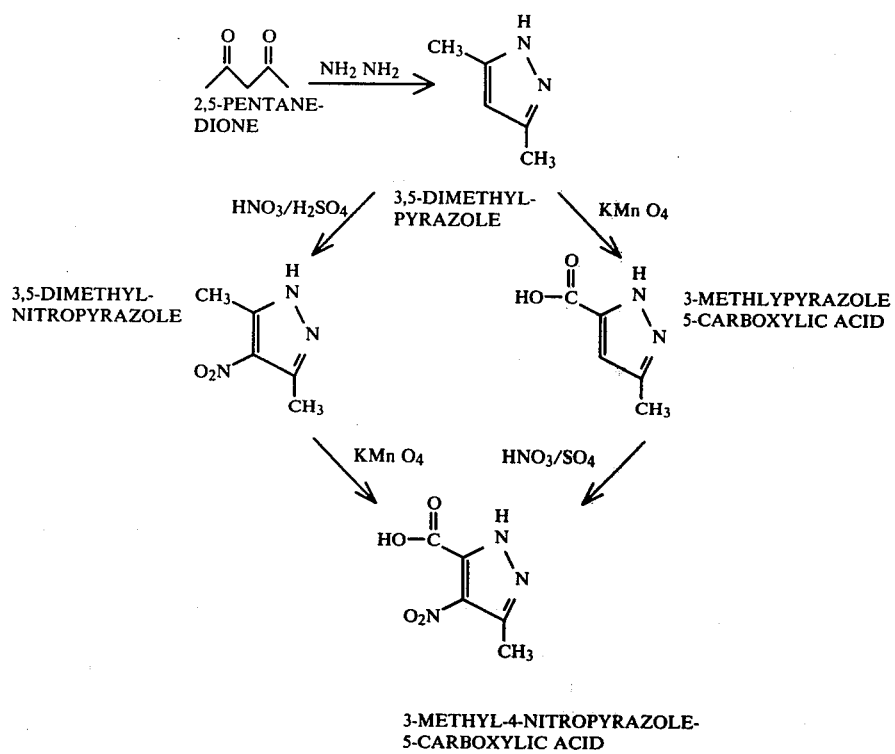

Transformation to ethyl 3-methyl-4-nitropyrazole-5-carboxylate

Esterification of 3-methyl-4-nitropyrazole-5-carboxylic acid was previously reported using ethanol and sulphuric acid at elevated temperatures. Attempts to repeat this procedure resulted in concomitant alkylation of the pyrazole nucleus. However, it was found that the desired ester could be obtained if this reaction was run at room temperature.

Esterification of this same acid is also reported using ethanol and hydrogen chloride, although no yield is stated. See Musante, C., *Gazz. Chim. Ital.*, 75, 121 (1945). Application of this method in the present case afforded the desired product in nearly quantitative yield. This reaction can be illustrated as follows:

3-methyl-4-aminopyrazole-5-carboxamide

The ester compound was transformed by reaction with ammonium hydroxide into an amide in 81–96% yield which is considerably higher than previously found. See Robbins, R. R., Holum, L. B. and Furcht, F. W., *J. Org. Chem.*, 21, 833 (1956). This reaction can be illustrated as follows:

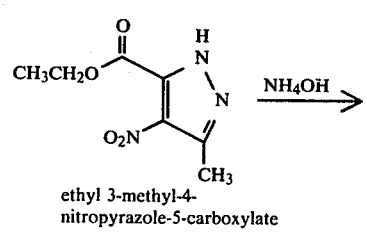

-continued

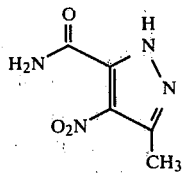

3-methyl-4-nitropyrazole-
5-carboxamide

Transformation to 4-formylamino-3-methylpyrazole-5-carboxamide

The compound 4-formylamino-3-methylpyrazole-5-carboxamide was prepared by catalytic reduction and formylation of the carboxamide compound. Hydrogen in the presence of palladium and carbon was used for the reduction and formylation was achieved with formic acid. The reduction and formylation steps were done simultaneously, but could be carried out as separate steps. The combined reactions are illustrated as follows:

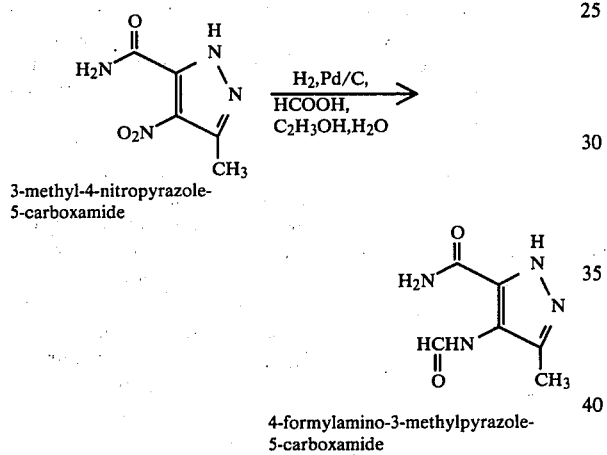

This new compound was isolated and found to melt at 213°–217°, and began to solidify around 260° C. and decomposed at about 340° C. It was characterized as 4-formylamino-3-methylpyrazole-5-carboxamide by nmr and mass spectroscopy. The melting behavior was theorized to be caused by thermal cyclization to 7-hydroxy-3-methylpyrazolo[4,3-d]pyrimidine which was confirmed by tlc.

Ring Closure 4-formylamino-3-methylpyrazole-5-carboxamide was cyclized in refluxing dimethylformamide with a catalytic amount of sodium methoxide to produce 7-hydroxy-3-methyl pyrazolo[4,3-d]pyrimidine in about an 80% yield. This reaction is illustrated as follows:

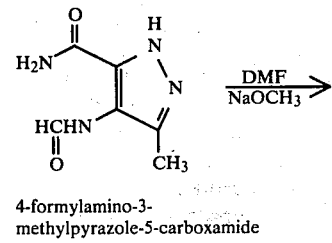

4-formylamino-3-
methylpyrazole-5-carboxamide

-continued

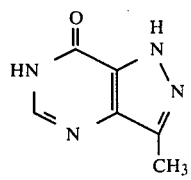

7-hydroxy-3-methylpyrazolo-
[4,3-d]pyrimidine

Ring closure is thus achieved in this synthetic scheme by an intramolecular mechanism rather than an intermolecular mechanism as is the case in prior processes. This results in a much higher yield of product which is significantly purer than that produced by intermolecular routes.

Transformation to 7-chloro analogue

The 7-chloro analogue was prepared by reacting the 7-hydroxy compound with N,N-diethylaniline and phosphorous oxychloride with stirring. This reaction is illustrated as follows:

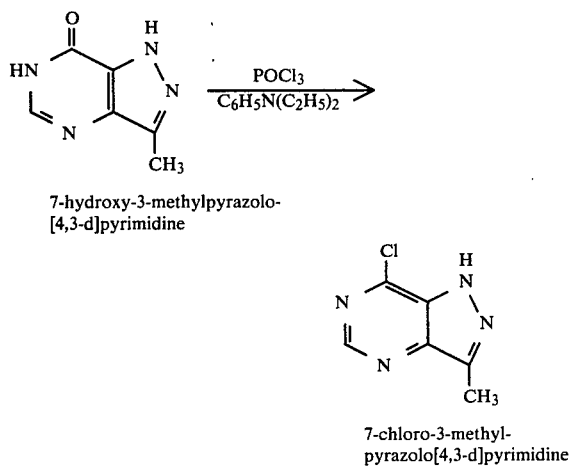

Preparation of alkylamino substituents

An alkylamine is added to the 7-chloro compound and this produces an exothermic reaction which on cooling gives a crude quantitative yield of the 7-alkylamino substituted compound. A pure material can be isolated in high yields easily. This reaction is illustrated for n-pentylamine as follows:

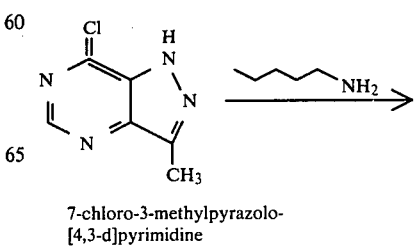

7-chloro-3-methylpyrazolo-
[4,3-d]pyrimidine

*-continued*

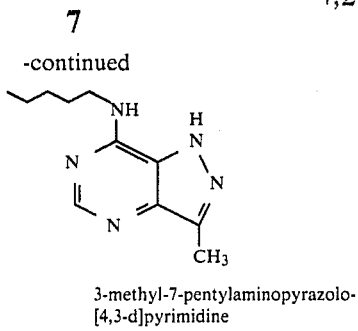

3-methyl-7-pentylaminopyrazolo-[4,3-d]pyrimidine

This invention can be further described by way of the following specific examples.

EXAMPLE 1

PREPARATION OF 3,5-DIMETHYLPYRAZOLE

To a stirred mixture of pentanedione (367.8 g, 3.76 mol) in 1000 ml water and 3 ml acetic acid, 85% hydrazine hydrate was added at a rate such that the temperature did not exceed 90°. After complete addition the reaction mixture was heated under reflux for 30 min. On cooling most of the product crystallized in colorless plates and was filtered off and washed with brine. Drying at 30°-40° in the vacuum oven afforded 274.9 g=77.8%. Extration of the mother liquor with ether (3×200 ml), drying of the combined extracts (sodium sulfate) and distillation of oil obtained after evaporation of the ether gave 34 g of starting material (b.p. 139°) and 7.2 g of dimethylpyrazole. Total yield: 277.9 g (~85%, based on consumed starting material).

Following the procedures described in Org. Synth. and Fitteon-Smiley yields of 67-71% were obtained compared with 73-76% cited in Fitteon-Smiley.

EXAMPLE 2

PREPARATION OF 3-METHYLPYRAZOLE-5-CARBOXYLIC ACID

A mixture of 3,5-dimethylpyrazole (5.19 g, 54 mmol) and potassium permanganate (9.0 g, 57 mmol) in water (40 ml) was heated on the steam bath until the purple color had practically disappeared (about 15 min.). The second portion of potassium permanganate (9.0 g, 57 mmol) was added slowly, allowing time for complete decolorization before each addition. A very exothermic reaction accompanied by some foaming occurred. The reaction mixture was filtered while hot and the maganese dioxide was washed with boiling water (4×20 ml). The filtrate was concentrated in vacuo and concentrated hydrochloric acid was added (5 ml), lowering the pH to 3-3.5. The reaction mixture was evaporated to dryness and exhaustive trituration with boiling, absolute ethanol afforded, after recrystallization from absolute ethanol, 5.1 g (75%) of the acid.

EXAMPLE 3

Nitration of 3-Methylpyrazole-5-Carboxylic Acid

The nitration was carried out by the method of Musante (*Gass. Chim. Ital.*, 75, 121 (1945). To a cooled stirred solution of 29.0 ml of fuming nitric acid and 43.5 g of 20% fuming sulfuric acid was added, in small portions, 29.55 g (234 mmol) of 3-methylpyrazole-5-carboxylic acid. The resulting solution was heated at about 70° for 6 hr. The cooled solution was treated with water and filtered. Recrystallization of the product from water afforded the product as colorless needles, yield 39.5 g (99%), mp 196°-8°.

EXAMPLE 4

Preparation of 3,5-Dimethyl-4-Nitropyrazole

To a solution of 3,5-dimethylpyrazole (86.5 g, 0.90 mol) in concentrated sulfuric acid (170 ml), conc nitric acid (103 ml, d=1.423) was added with stirring and icecooling. After one hour concentrated sulfuric acid (100 ml) was added slowly with stirring resulting in a temperature rise to 70°-80° C. After stirring overnight at 30°-35° C., the mixture was poured into ice (1.5 l) and neutralized with potassium hydroxide. Extraction with methylene chloride (3×350 ml), drying of the organic phase (Na$_2$SO$_4$) and evaporation gave off-white crystals which were dried in vacuo at 70°. Yield 106.2 g=83.6%, m.p. 125°.

EXAMPLE 5

Oxidation of 3,5-Dimethyl-4-Nitropyrazole

To a boiling solution of 3,5-dimethyl-4-nitropyrazole (106.2 g, 0.752 mol) in one liter of water in a 5-liter 3-necked round-bottomed flask was added potassium permanganate (261.4 g, 1.65 mol, 2.2 equiv.) with vigorous, mechanical stirring. After the addition was complete, the reaction mixture was heated to boiling for another 10 min. and filtered while hot. The precipitated MnO$_2$ was washed with boiling water (2×200 ml) and the lime-green filtrate was acidified with concentrated hydrochloric acid (60 ml), whereupon the product crystallized as needles. The solution was allowed to stand overnight in the refrigerator and then filtered and the crystals washed with ice-water. The solution was allowed to stand overnight in the refrigerator and then filtered and the crystals washed with ice-water. 115 g of hydrated product (95% based on consumed starting material). From the mother liquor 15.4 g of starting material could be recovered. The material was dried in vacuo at 110° to remove the water of hydration.

EXAMPLE 6

Preparation of Ethyl 3-Methyl-4-Nitropyrazole-5-Carboxylate

A solution of 3-methyl-4-nitropyrazole-5-carboxylic acid (70.4 g, 0.41 mol) in ethanol (300 ml) was saturated with hydrogen chloride prepared from the combination of concentrated hydrochloric acid (430 ml) and concentrated sulphuric acid (430 ml) at 0°. After standing overnight at room temperature, the reaction mixture was evaporated to dryness yielding 77.1 g (94%) of an oil which crystallized after seeding, m.p. 81°-86°.

EXAMPLE 7

Preparation of 3-Methyl-4-Nitropyrazole-5-Carboxamide

Ethyl 3-methyl-4-nitropyrazole-5-carboxylate (82.5 g, 0.41 mol) was heated at reflux in 600 ml of concentrated ammonium hydroxide for 2 hours. Concentrated ammonium hydroxide (100 ml) was added and the solution was heated at reflux for an additional three hours. The solution was concentrated in vacuo until the product began to crystallize. The crude material was recrystallized from 700 ml of water to give 47 g product, m.p. 218°-220° (decomp). From the mother liquor was recovered 25 g of 3-methyl-7-nitropyrazole-5-carboxylic acid. Based on the amount of nitro acid consumed, the yield was 95.8%.

EXAMPLE 8

Preparation of 4-Formylamino-3-Methylpyrazole-5-Carboxamide

A mixture of 3-methyl-4-nitropyrazole-5-carboxamide (17.0 g, 0.1 mol) in a mixture of 20 ml of 97–100% formic acid, 160 ml of ethanol and 30 ml of water was hydrogenated overnight at 40°–60° using 150 mg of 5% palladium-on-charcoal at 50 psi. Filtration of the hot solution through Celite and evaporation gave 17.8 g of crude, ochre-colored product which was recrystallized from ethanol: 1st crop 9.3 g colorless, 2nd crop 6.7 g brownish, total yield, 16.0 g (95%).

EXAMPLE 9

Preparation of 3-Methyl-7-Hydroxypyrazolo[4,3-d]Pyrimidine

A solution of 4-formylamino-3-methylpyrazole-5-carboxamide (21.0 g, 125 mmol) and sodium methoxide (about 30 mg) in dimethylformamide (42 ml) was heated at reflux for 6 hrs. in an oil bath maintained at 160°. Some product crystallized in the hot reaction mixture. Cooling, filtering and washing with ethanol afforded (after drying in a vacuum oven at 120°) 15.03 g (80.2%) of a white solid, m.p. 340°.

EXAMPLE 10

Preparation of 7-Chloro-3-Methylpyrazolo[4,3-d]Pyrimidine

A mixture of 3-methyl-7-hydroxypyrazolo[4,3-d]pyrimidine (1.0 g, 6.6 mmol), N,N-diethylaniline (2.0 g) and phosphorous oxychloride (16.5 g) was heated with magnetic stirring in an oil bath. The temperature was raised from 55° to 78° over the course of 40 min. At this point, all of the starting material had dissolved and the solution had turned red. The excess $POCl_3$ was distilled off in vacuo (this procedure took 15 min.) and ice-water (50 ml) was added to the residue. The resulting red solution was saturated with sodium chloride (12 g) whereupon it turned yellow. The solution was extracted with ethyl acetate (4×40 ml) and the combined extract was filtered through alumina (5 g; 80–325 mesh), washed with brine (40 ml), dried ($Na_2SO_4$) and evaporated, yielding 0.83 g (74%) of eggshell colored crystals.

EXAMPLE 11

Preparation of 3-Methyl-7-n-Pentylaminopyrazolo [4,3-d]Pyrimidine

When n-pentylamine (7 g) was added to 7-chloro-3-methylpyrazolo[4,3-d]pyrimidine (6.13 g, 36 mmol), an exothermic reaction took place and the mixture heated itself to boiling. The cooled reaction mixture was triturarted with water (100 ml). The crude product crystallized and was filtered, washed with water and air-dried to give a quantitative crude yield of slightly yellow crystals. Recrystallization from ether and treatment with charcoal afforded the product, yield 5.0 g (63%), m.p. 157.5°–158.5°. An additional 1.24 g was recovered from the mother liquor as the maleinate. Total yield, 73.6%.

Those skilled in the art will recognize, or be able to ascertain using no more than routine experimentation, other equivalents for the specific transformations, reactants, catalysts, etc. described herein. Such equivalents are intended to be included within the scope of the following claims.

What is claimed is:

1. In a method for synthesizing 7-alkylamino-3-methylpyrazolo[4,3-d]pyrimidines, including the steps of esterifying 3-methyl-4-nitropyrazole-5-carboxylic acid to ethyl 3-methyl-4-nitropyrazole-5-carboxylate, forming 3-methyl-4-nitropyrazole-5-carboxamide from ethyl 3-methyl-4-nitropyrazole-5-carboxylate, catalytically reducing and formylating ethyl 3-methyl-4-nitropyrazole-5-carboxamide to produce 4-formylamino-3-methylpyrazole-5-carboxamide, closing the ring of 4-formylamino-3-methylpyrazole-5-carboxamide to produce 3-methyl-7-hydroxypyrazolo[4,3-d]pyrimidine, chlorinating said 3-methyl-7-hydroxypyrazolo [4,3-d]pyrimidine to produce 7-chloro-3-methylpyrazolo-[4,3-d], and reacting said 7-chloro-3-methylpyrazolo[4,3-d]pyrimidine with an alkylamine to produce a 7-alkylamino-3-methylpyrazolo[4,3-d]pyrimidine:

the improvement wherein ethyl 3-methyl-4-nitropyrazole-5-carboxamide is simultaneously catalytically reduced and formylated to produce 4-formylamino-3-methylpyrazole-5-carboxamide and the ring of 4-formylamino-3-methylpyrazolo-5-carboxamide is intramolecularly closed to produce 3-methyl-7-hydroxypyrazolo[4,3-d].

2. The improvement of claim 1 wherein said alkylamine comprises n-pentylamine.

3. The improvement of claim 1 wherein 3-methyl-4-nitropyrazole-5-carboxylic acid is produced by first condensing 2,5-pentanedione with hydrazine hydrate to from 3,5-dimethyl-pyrazole and subsequently oxidizing and nitrating said 3,5-dimethylpyrazole-5-carboxylic acid.

4. A method of claim 3 wherein said alkylamine comprises n-pentylamine.

* * * * *